United States Patent [19]

Gehret et al.

[11] Patent Number: 4,732,899
[45] Date of Patent: Mar. 22, 1988

[54] (DI)ALKOXYCARBONYLAMINO-S-TRIAZINE DERIVATIVES AND THE USE THEREOF AGAINST PESTS WHICH ARE PARASITES OF DOMESTIC ANIMALS AND CULTIVATED PLANTS

[75] Inventors: Jean-Claude Gehret, Aesch; Odd Kristiansen, Möhlin, both of Switzerland

[73] Assignee: Ciba-Geigy Corporation, Ardsley, N.Y.

[21] Appl. No.: 934,299

[22] Filed: Nov. 24, 1986

[30] Foreign Application Priority Data

Dec. 2, 1985 [CH] Switzerland .......................... 5130/85

[51] Int. Cl.$^4$ ............................................. A01N 43/68
[52] U.S. Cl. ..................................... 514/245; 544/196; 544/197
[58] Field of Search .................. 544/196, 197; 514/245

[56] References Cited

U.S. PATENT DOCUMENTS

| | | | |
|---|---|---|---|
| 4,007,032 | 2/1977 | Berrer et al. | 71/93 |
| 4,187,304 | 2/1980 | Immler et al. | 514/245 |
| 4,187,305 | 2/1980 | Immler et al. | 514/365 |
| 4,225,598 | 9/1980 | Brechbühler et al. | 514/245 |
| 4,402,954 | 9/1983 | Laanio et al. | 514/245 |
| 4,490,372 | 12/1984 | Laanio et al. | 514/245 |
| 4,563,457 | 1/1986 | Laanio et al. | 514/245 |

FOREIGN PATENT DOCUMENTS 0145660 of 1984 European Pat. Off. .

OTHER PUBLICATIONS

Chemical Abstracts, C.A. 82:72946d, (1975).

Primary Examiner—Henry R. Jiles
Assistant Examiner—Zinna Northington
Attorney, Agent, or Firm—Edward McC. Roberts; Meredith C. Findlay

[57] ABSTRACT

The invention relates to (di)alkoxycarbonylamino-s-triazine derivatives and their sulfureous representatives of formula I

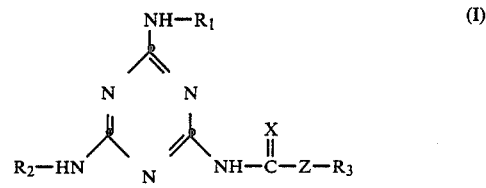

wherein $R_1$ is $C_3$–$C_6$alkyl or $C_3$–$C_6$cycloalkyl;

$R_2$ is hydrogen, $C_1$–$C_6$alkyl, $C_3$–$C_6$cycloalkyl or the group —C(X)—$ZR_3$;

$R_3$ is $C_1$–$C_6$haloalkyl, $C_2$–$C_4$alkenyl or $C_2$–$C_4$haloalkenyl;

X is oxygen or sulfur; and

Z is oxygen or sulfur;

and to the acid addition salts thereof. The invention also relates to the preparation of said compounds from the diamino-s-triazines on which they are based and to the use thereof against pests which are pathogens of domestic animals and cultivated plants.

11 Claims, No Drawings

(DI)ALKOXYCARBONYLAMINO-S-TRIAZINE DERIVATIVES AND THE USE THEREOF AGAINST PESTS WHICH ARE PARASITES OF DOMESTIC ANIMALS AND CULTIVATED PLANTS

The present invention relates to (di)alkoxycarbonylamino-s-triazine derivatives and their sulfureous representatives of formula I below, to their preparation and to the use thereof against parasites endoparasite and ectoparasite and insects which are pathogens of domestic animals or cultivated plants, as well as to pesticidal compositions which contain at least one of these compounds as active ingredient.

Accordingly, the present invention relates to compounds of formula I

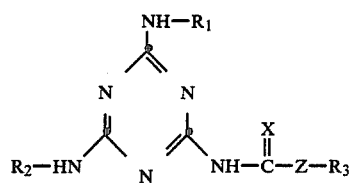

wherein
$R_1$ is $C_3-C_6$alkyl or $C_3-C_6$cycloalkyl;
$R_2$ is hydrogen, $C_1-C_6$alkyl, $C_3-C_6$cycloalkyl or the group $-C(X)-ZR_3$;
$R_3$ is $C_1-C_6$alkyl, $C_1-C_6$haloalkyl, $C_2-C_4$alkenyl or $C_2-C_4$haloalkenyl;
X is oxygen or sulfur; and
Z is oxygen or sulfur;
and to the acid addition salts thereof.

Depending on the number of indicated carbon atoms, alkyl by itself or as moiety of another substituent shall be understood as meaning for example the following straight chain groups: methyl, ethyl, propyl, butyl, pentyl and hexyl, and also the branched isomers thereof, e.g. isopropyl, isobutyl, tert-butyl, sec-butyl, isopentyl etc. Alkenyl is e.g. vinyl, 1-propenyl, allyl, 1-butenyl, 2-butenyl, 3-butenyl etc. The prefix "halo" signifies that the corresponding substituent is substituted by one or more identical or different halogen atoms. Examples of haloalkyl are: $CCl_3$, $CF_3$, $CBr_3$, $CHCl_2$, $CHF_2$, $CHBr_2$, $CH_2Cl$, $CH_2F$, $CH_2Br$, $CHClF$, $CFClBr$, $C_2F_5$, $C_2Cl_5$, $CH_2CF_3$, $C(CH_3)_2CF_3$ etc. Examples of haloalkenyl are: $CCl_2=CCl_2$, $CH_2=CCl_2$, $CF_2=CF_2$, $CH_2=CF_2$, $CHCl=CCl_2$, $CHCl=CClF$, $CH_2-CH=CCl_2$ etc. Cyloalkyl is e.g. cyclopropyl, cyclobutyl, cyclopentyl or cyclohexyl.

Acid addition salts of compounds of formula I shall be understood as meaning the addition salts of inorganic and organic acids which are formed by addition of an equivalent amount of a salt-forming acid to the basic molecule.

Examples of salt-forming acids are inorganic acids: hydrohalic acid such as hydrofluoric acid, hydrochloric acid, hydrobromic acid or hydriodic acid, as well as sulfuric acid, phosphoric acid, phosphorous acid and nitric acid; and organic acids, e.g. acetic acid, trifluoroacetic acid, trichloroacetic acid, propionic acid, glycolic acid, thiocyanic acid, lactic acid, succinic acid, citric acid, formic acid, benzenesulfonic acid, p-toluenesulfonic acid, methane-sulfonic acid, salicylic acid, p-aminosalicylic acid, phthalic acid, 2-phenoxybenzoic acid or 2-acetoxybenzoic acid.

At room temperature the compounds of formula I are mainly stable solids with a melting point in the range from about 50° to about 220° C. They have very valuable parasiticidal properties and can be used curatively and preventively for controlling a series of parasites of domestic animals and cultivated plants, and for controlling insects, in particular Diptera larvae. Compared with other triamino-s-triazine derivatives, the compounds of formula I have the advantage that, when applied to productive livestock, they are in the main excreted in the faeces where their intensive larvicidal activity prevents the parasite from spreading. In the case of customary triamino-s-triazines, a large part of the active substance is lost through urine discharge.

The following groups of compounds of formula I are preferred on account of their pronounced activity:
(a) compounds of formula I, wherein
$R_1$ is $C_3$alkyl or cyclopropyl;
$R_2$ is hydrogen, $C_1-C_3$alkyl, cyclopropyl or C(O)$OR_3$;
$R_3$ is $C_1-C_4$alkyl, $C_1-C_4$chloroalkyl, $C_2-C_4$alkenyl or $C_2-C_4$haloalkenyl; and
X and Z are oxygen;
(b) compounds of formula I, wherein
$R_1$ is isopropyl or cyclopropyl;
$R_2$ is hydrogen or $C_1-C_3$alkyl;
$R_3$ is methyl, ethyl, n-propyl, n-butyl or $C_2-C_4$alkenyl; and
X and Z are oxygen.

Examples of preferred individual substances are:
2-cyclopropylamino-4-amino-6-allyloxycarbonylamino-s-triazine and the acid addition salts thereof,
2-isopropylamino-4-amino-6-allyloxycarbonylamino-s-triazine and the acid addition salts thereof,
2-cyclopropylamino-4-amino-6-methoxycarbonylamino-s-triazine and the acid addition salts thereof,
2-cyclopropylamino-4-amino-6-ethoxycarbonylamino-s-triazine and the acid addition salts thereof,
2-cyclopropylamino-4-amino-6-n-butoxycarbonylamino-s-triazine and the acid addition salts thereof,
with the hydrochloric acid addition salts being of particular interest.

The compounds of formula I are prepared by reacting a compound of formula II

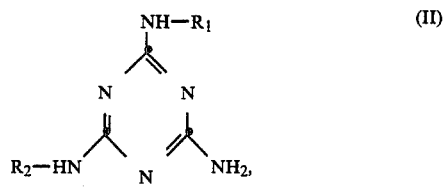

preferably in the presence of a base, with a sufficient amount of a reactive acid derivative of an acid of formula III

at a temperature in the range from 0° to 50° C., preferably from 15° to 30° C., and keeping the resultant reaction mixture for about 5 to 12 hours at a temperature in the range from 10° to 100° C., in which formulae II and III the substituents $R_1$, X, Z and $R_3$ are as defined for formula I and $R_2$ is hydrogen, $C_1$-$C_6$alkyl or $C_3$-$C_6$cycloalkyl.

Reactive acid derivatives of an acid of formula III are for example the anhydride or a halide thereof, in particular the chloride or bromide. The term "a sufficient amount" is to be regarded as the amount of reactive acid derivative which yields the desired product, i.e. in such cases where $R_2$ is hydrogen, $C_1$-$C_6$alkyl or $C_3$-$C_6$cycloalkyl and only one of the $NH_2$ groups is to be substituted, then 1 equivalent or a slight excess of the acid derivative of formula III is employed, whereas in such cases where $R_2$ is —C(X)—$ZR_3$ and both $NH_2$ groups are to be substituted, it is recommended to employ 2 equivalents or a slight excess of the acid derivative of formula III. In general, the reaction is carried out by dissolving the derivative of formula III (about 1.1 eq. when $R_2$=H, $C_1$-$C_6$alkyl or $C_3$-$C_6$cycloalkyl and about 2.2 eq. when $R_2$=—C(X)—$ZR_3$) in a small amount of solvent, then, at a temperature in the range from 0° to 50° C., preferably from 15° to 30° C., slowly adding the resultant solution dropwise to a mixture of a compound of formula II, a base and an inert solvent or mixture of solvents, and leaving the batch for several hours until completion of the reaction, e.g. overnight at a temperature in the range from 10° to 100° C., preferably from 15° to 30° C. when $R_2$=H, $C_1$-$C_6$alkyl or $C_3$-$C_6$cycloalkyl and preferably from 40° to 80° C. when $R_2$=C(X)—$ZR_3$. When the reaction is complete, the reaction mixture is allowed to reach room temperature, the solid precipitates are filtered off, and the solvent is removed, e.g. in vacuo. The residue is taken up in a customary organic solvent, the resultant solution is washed with water and saturated sodium chloride solution, dried over a suitable drying agent (e.g. sodium sulfate or magnesium sulfate) and filtered, and the filtrate is concentrated. After removal of the solvent, the product can be purified by conventional methods, e.g. by dissolution in a solvent and subsequent precipitation with another solvent. Chromatographic purification methods may also be employed.

In principle, all inert solvents customarily employed for acylation reactions are suitable for the reaction of a compound of formula II with a compound of formula III. Examples of such solvents are aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile, propionitrile; N-N-dialkylated amides such as dimethylformamide; dimethyl sulfoxide; ketones such as acetone, diethyl ketone, methyl ethyl ketone; and mixtures of such solvents with one another.

Suitable bases are both organic and inorganic bases, e.g. tertiary amines such as trialkylamines (trimethylamine, triethylamine, tripropylamine, diisopropylethylamine etc.), pyridine and pyridine bases (4-dimethylaminopyridine, 4-pyrrolidylaminopyridine etc.), N-methylpyrrolidone etc., as well as oxides, hydroxides, carbonates and bicarbonates of alkali metals and alkaline earth metals, and also alkali metal acetates.

The starting materials of formula II and the acids of formula III and their reactive derivatives are generally known or they can be prepared by methods analogous to those for preparing the known representatives.

Surprisingly, it has been found that the compounds of formula I have a pronounced larvicidal action against Dipter larvae. The compounds of formula I are effective in particular against the juvenile stages of the insects. The action results in the egg larvae dying and in the adults being prevented from hatching from the pupae. The action of the compounds of formula I is not to be compared with the mode of action of conventional insecticides, chemosterilants and juvenile hormone analogues.

The compounds of formula I are employed for controlling ectoparasites of domestic animals, and hygiene pests, in particular of the order Diptera and the families Culicidae, Simuliidae, Tipulidae, Muscidae and Calliphoridae. The compounds of formula I are particularly effective against larvae of the blowfly (*Lucilia sericata* and *Lucilia cuprina*) belonging to the family Calliphoridae, and also against fly larvae and mosquito larvae.

The compounds of formula I are also effective against representatives of the orders Siphonaptera (e.g. bloodsucking fleas).

In addition to their action against mosquitos and fleas, e.g. *Aëdes aegypti* and *Musca domestica,* compounds of formula I can also be successfully employed for controlling plant-destructive feeding insects in crops of ornamentals and useful plants, in particular in rice crops (e.g. aganist *Nilaparvata lugens* and *Nephotettix cincliceps*).

The compounds of formula I have an activity spectrum which, extending beyond the larval stage, also embraces the remaining development stages of the parasites, as well as the oviposition of fertile eggs.

Moreover, in a completely surprising manner, the compounds of formula I are distinguished by a prolonged biological action, which represents a particular feature of these compounds. Depending on the mode of application, this prolonged mode of action can extend over a period of 3 months, which provides many advantages over known preparations.

When the compound of this invention are used for livestock-building hygiene, their prolonged action makes it possible, for example, to achieve an extremely low frequency of application, so that in moderate climatic regions with a 3-month summer season a single application is sufficient to reduce on a long-term basis in livestock buildings the development of the harmful Diptera larvae, which is normally promoted by the climatic conditions.

In the treatment of grazing animals with the compounds of this invention, for example by means of cattle dips, pour-on methods or spray races, the surprising adhesive action of the active substances provides a long-lasting toxic effect against ectoparasites, e.g. harmful Diptera, on the skin and fur of the animals. This prevents the active substances which have been applied to the skin or fur of productive livestock from being prematurely washed out or washed off by rainwater as it drips off of the animals.

The particular advantages of the sustained action of the compounds of formula I becomes manifest especially in the case of oral administration to productive livestock. In this application process, the active substances exhibit an effective and prolonged insecticidal activity, in particular in the excreted faeces. Consequently, infestation by harmful insects, in particular Diptera, can be prevented before the pests occur in the vicinity of the animals, e.g. in livestock buildings, in enclosures and on grazing land, since the Diptera larvae hatching out of the deposited eggs are killed immediately. A particularly important feature of this special form of application is that, by virtue of their structural properties, the compounds of formula I are physiologically indifferent to warm-blooded animals. This method of selectively controlling the proliferation of insects is considerably more efficient and at the same time more economical than the customary methods of treating livestock buildings and enclosures on a large scale.

For controlling pests, the compounds of formula I can be used by themselves or in the form of compositions which also contain suitable carriers and adjuvants, or mixtures of such substances. Suitable carriers and formulation assistants may be solid or liquid and correspond to the substances conventionally employed in the art of formulation, e.g. natural or regenerated substances, solvents, dispersants, wetting agents, tackifiers, thickeners or binders.

For application, the compounds of formula I are processed to dusts, emulsifiable concentrates, granulates, dispersions, sprays, baits, premixtures, solutions or suspensions in customary formulations by methods generally known in the art of application.

If the compounds of formula I are administered orally to productive livestock, then convenient rates of application are 0.1 to 1000 mg/kg, preferably 2 to 100 mg/kg, of body weight. However, if these substances are applied topically to the productive livestock, favourable concentrations are 1 to 5000 ppm, preferably 100 to 1000 ppm. If the substances of this invention are employed in the field of hygiene or for plant protection and therefore have to be applied to specific areas, then it is advantageous to employ concentrations of 1 to 1000 ppm, preferably 10 to 500 ppm.

The compositions of this invention are prepared in a manner known per se by homogeneously mixing and/or grinding the compounds of formula I with suitable carriers, with or without the addition of dispersants or solvents which are inert to said compounds of formula I. The compounds can be processed to the following formulations and applied as such:

solid formulations: dusts, scattering agents, granulates, premixes, baits, (coated granulates, impregnated granulates and homogeneous granulates);
liquid formulations:
  (a) water-dispersible concentrates: wettable powders, pastes, emulsions;
  (b) solutions: pour-on solutions and sprays.

The content of active ingredient in the above formulations is from 0.1 to 95.0% by weight, preferably from 1 to 80% by weight.

On account of the many possible formulations, the compounds of formula I of the invention, as active ingredients of compositions, are suitable for controlling, in a great variety of ways, parasites on or in the vicinity of animals, e.g. in livestock buildings. The compounds of formula I can thus be applied for example in cattle dips, spray races, pour-on solutions or hand sprays. They can also be used with great success for treating animal faeces by feed-through methods, and for the hygienic treatment of manure in livestock buildings.

PREPARATORY EXAMPLES

EXAMPLE P1

Preparation of 2-cyclopropylamino-4,6-bis-isobutoxycarbonylamino-s-triazine 16.4 g (0.12 mol) of isobutyl chloroformate are added dropwise to a mixture of 8.3 g (0.05 mol) of 2,4-diamino-6-cyclopropylamino-s-triazine, 0.5 g of 4-dimethylaminopyridine and 125 ml of pyridine. The batch is stirred for 1 hour at room temperature and then for 1 hour at 55°-60° C. After the precipitate has been filtered off, the reaction mixture is concentrated by evaporation in a water-jet vacuum, the residue is taken up in 150 ml of chloroform and extracted with 100 ml of water. After drying over sodium sulfate, the solvent is distilled off, and the crude product is purified by column chromatography through silica with methylene chloride as eluant.

Yield: 6.2 g of the product; m.p.: 146°-147° C.

EXAMPLE P2

Preparation of 2-cyclopropylamino-4-amino-6-allyloxycarbonylamino-s-triazine

Over 4 hours, a solution of 6.6 g (0.055 mol) of allyl chloroformate in 50 ml of dioxane is slowly added dropwise at room temperature to a mixture of 6.6 g (0.05 mol) of 2,4-diamino-6-cyclopropylamino-3-triazine, 5.1 g (0.05 mol) of triethylamine and 300 ml of dioxane. The batch is then stirred overnight at room temperature. After the precipitate has been filtered off, the reaction mixture is concentrated by evaporation in a water-jet vacuum, the residue is taken up in 400 ml of tetrahydrofuran and extracted with 200 ml of water and 150 ml of saturated sodium chloride solution. After drying over magnesium sulfate, the solvent is removed by evaporation. The residue is taken up in 50 ml of acetone. With good stirring, the product is precipitated with ethyl acetate, isolated by filtration and dried.

Yield: 8.8 g; m.p.: 168°-171° C.

EXAMPLE P3

Preparation of 2-cyclopropylamino-4-amino-6-allyloxycarbonylamino-s-triazine hydrochloride 250 mg (1 mmol) of the free base are dissolved at room temperature in 0.55 ml (1.1 mmol) of aqueous 2n hydrochloric acid, and the resultant solution is stirred vigourously for 10 minutes and subsequently evaporated to dryness under a high vacuum. The amorphous hydrochloride salt formed melts above 68° C.

The following compounds of formula I, inter alia, can also be prepared by procedures analogous to those described above.

TABLE 1

Compounds of formula I $$\text{R}_2\text{-HN}-\underset{N}{\overset{N}{\underset{\|}{\diagdown}}}\overset{NH-R_1}{\underset{}{\diagup\diagdown}}\underset{N}{\overset{N}{\diagdown\diagup}}-NH-\overset{\overset{X}{\|}}{C}-Z-R_3 \quad (I)$$

| Comp. | $R_1$ | $R_2$ | $-\overset{\overset{X}{\|}}{C}-ZR_3$ | Salt | Physical data [°C.] |
|---|---|---|---|---|---|
| 1.1 | cyclopropyl | $CO-OCH_3$ | $CO-OCH_3$ | — | m.p. 75–80 |
| 1.2 | cyclopropyl | H | $CO-OCH_3$ | — | m.p. 152–155 |
| 1.3 | cyclopropyl | H | $CO-OCH_3$ | HCl | m.p. from 98 dec. |
| 1.4 | cyclopropyl | $CO-OCH_2CH=CH_2$ | $CO-OCH_2CH=CH_2$ | — | m.p. 68–70 |
| 1.5 | cyclopropyl | $CO-OCH_2CH=CH_2$ | $CO-OCH_2CH=CH_2$ | HCl | m.p. 65–68 |
| 1.6 | cyclopropyl | $CO-OC_2H_5$ | $CO-OC_2H_5$ | — | m.p. 93–97 |
| 1.7 | cyclopropyl | $CO-OC_2H_5$ | $CO-OC_2H_5$ | HCl | m.p. 55–60 |
| 1.8 | cyclopropyl | H | $CO-OC_2H_5$ | — | m.p. 208–210 |
| 1.9 | cyclopropyl | H | $CO-OC_2H_5$ | HCl | m.p. 108–113 |
| 1.10 | cyclopropyl | H | $CO-OCH_2CH=CH_2$ | — | m.p. 178–182 |
| 1.11 | cyclopropyl | H | $CO-OCH_2CH=CH_2$ | HCl | m.p. 63–68 |
| 1.12 | cyclopropyl | $CO-OC_2H_5$ | $CO-OC_2H_5$ | HBr | m.p. from 90 dec. |
| 1.13 | cyclopropyl | H | $COC_4H_9-n$ | — | m.p. 184–185 |
| 1.14 | cyclopropyl | $CO-OCH_2CH(CH_3)_2$ | $CO-OCH_2CH(CH_3)_2$ | — | m.p. 146–147 |
| 1.15 | cyclopropyl | $CO-OC_4H_9-n$ | $CO-OC_4H_9-n$ | — | m.p. 127–129 |
| 1.16 | cyclopropyl | $CO-OC(CCl_3)(CH_3)_2$ | $CO-OC(CCl_3)(CH_3)_2$ | — | m.p. from 155 dec. |
| 1.17 | cyclopropyl | H | $CO-OC(CH_3)_2CCl_3$ | — | |
| 1.18 | cyclopropyl | H | $CO-OC(CH_3)_2CCl_3$ | HCl | |
| 1.19 | cyclopropyl | H | $CO-OC_4H_9-i$ | — | |
| 1.20 | cyclopropyl | H | $CO-OC_4H_9-i$ | HCl | |
| 1.21 | i-propyl | H | $CO-OCH_3$ | — | |
| 1.22 | i-propyl | H | $CO-OCH_3$ | HCl | |
| 1.23 | i-propyl | cyclopropyl | $CO-OC_2H_5$ | — | |
| 1.24 | i-propyl | cyclopropyl | $CO-OC_2H_5$ | HCl | |

[dec. = decomposition]

EXAMPLE B1

Action against *Lucilia sericata*

Freshly deposited eggs of the blowfly (*L. sericata*) are placed in small portions (30–50 eggs) into each of a number of test tubes, in which 4 ml of nutrient medium have been mixed with 1 ml of test solution in the intermediate dilution required for the final concentration. After inoculation of the culture medium, the test tubes are closed with cotton-wool plugs and are then incubated in an incubator at 30° C. for 4 days. In the untreated medium serving as a control, larvae about 1 cm in length (stage 3) have developed by the end of this 4-day period. When a substance is active, by the end of this period the larvae are either dead or moribund and clearly retarded. Tests are carried out simultaneously with concentrations of 100 to 0.01 ppm. The lowest fully effective concentration (LC 100) is taken as a measure of effectiveness.

The test embraces substances which are effective as contact poisons and also those substances which are effective as stomach poisons. Repellency is also taken into account since this causes the larvae to migrate from the medium and consequently to starve to death.

Most of the compounds of formula I of Table 1 are fully effective at concentrations of 0.1 to 5.0 ppm, most preferred in this context are the compounds 1.3, 1.5, 1.10, 1.11 and 1.13.

EXAMPLE B2

Action against *Lucilia cuprina*

Freshly deposited eggs of the blowfly (*L. cuprina*) are placed in small portions (30–50 eggs) into each of a number of test tubes, in which 4 ml of nutrient medium have been mixed with 1 ml of test solution in the intermediate dilution required for the final concentration. After inoculation of the culture medium, the test tubes are closed with cotton-wool plugs and are then incubated in an incubator at 30° C. for 4 days. In the untreated medium serving as a control, larvae about 1 cm in length (stage 3) have developed by the end of this 4-day period. When a substance is active, by the end of this period the larvae are either dead or moribund and clearly retarded. Tests are carried out simultaneously with concentrations of 100 to 0.01 ppm. The lowest fully effective concentration (LC 100) is taken as a measure of effectiveness.

The test embraces substances which are effective as contact poisons and also those substances which are effective as stomach poisons. Repellency is also taken into account since this causes the larvae to migrate from the medium and consequently to starve to death.

Most of the compounds of Table 1 are fully effective at concentrations of 0.1 to 5.0 ppm, preferred in this context are the compounds 1.3, 1.8, 1.9, 1.10 and 1.11.

EXAMPLE B3

Action against *Aëdes aegypti*

A 0.1% solution of the test compound in acetone is pipetted onto the surface of 150 ml of water in beakers in amounts sufficient to give concentrations of 10, 5 and 1 ppm. After the acetone has evaporated, 50 to 100 3-day-old Aëdes larve are put into each beaker. The mortality rate is determined after 1 and 8 days.

Some compounds of Table 1 effect 100% mortality of the larvae at concentrations between 5 and 10 ppm.

EXAMPLE B4

Action against *Nilaparvate lugens* (nymphs) and *Nephotettix cincliceps*

The test is carried out with growing rice plants. For this purpose 10 plants (thickness of stem 8 mm) about 20 cm in height are planted into each of a number of pots (diameter 5.5 cm). The plants on each pot are sprayed on a rotary table with 50 ml of an aqueous solution containing 400 or 800 ppm of the formulated test compound. After the spray coating has dried, each plant is populated with 20 nymphs of the test organisms in the third stage. To prevent the cicadas from escaping, a glass cylinder is slipped over each of the plants and sealed with a gauze top. The nymphs are kept for over 6 days on the treated plant until the adult stage has been reached. The mortality rate is determined 6 days after treatment.

Compounds of Table 1 exhibit good activity against larvae of *Nilaparvata lugens* and of *Nephotettix cincliceps*.

FORMULATION EXAMPLES

The compounds of formula I can be formulated for example as follows:

Granulate 5 parts of a compound of Table 1
0.25 parts of epoxidised vegetable oil
0.25 parts of cetyl polyglycol ether,
3.50 parts of polyethylene glycol
91 parts of kaolin (particle size 0.3–0.8 mm).

The active ingredient and the epoxidised vegetable oil are dissolved in 6 parts of acetone, and polyethylene glycol and cetyl polyglycol ether are then added. The resultant solution is sprayed onto kaolin, and the acetone is subsequently evaporated off in vacuo. Granulates of this type can be added to the animal feed.

Dust 5 parts by weight of a finely ground compound of Table 1 are thoroughly mixed with
2 parts by weight of a precipitated silicic acid and
93 parts by weight of talcum.

The active ingredient is homogeneously mixed with the carriers, and the mixture is ground. The dust can not only be used externally but can also be added to the animal feed.

Wettable powder 5 to 30 parts by weight of a compound of Table 1 are thoroughly mixed, in a mixing apparatus, with
5 parts by weight of an absorbent carrier (silicic acid K 320 or Wessalon S) and
55 to 80 parts by weight of a carrier [bolus alba oder kaolin (B 24)] and a dispersant mixture consisting of
5 parts by weight of sodium lauryl sulfonate and
5 parts by weight of an alkylaryl polyglycol ether.

This mixture is ground in a pinned disk mill or an air jet mill to a particle size of 5–15 μm. The wettable powder thus obtained gives a good suspension in water.

Emulsifiable concentrate 20 parts by weight of a compound of Table 1 are dissolved in
70 parts by weight of xylene, and to the solution are added
10 parts by weight of an emulsifier consisting of a mixture of an alkylphenyl polyglycol ether and calcium dodecylbenzenesulfonate.

The emulsifiable concentrate can be diluted in any ratio with water, thereby forming a milky emulsion which can be added to the liquid feeds.

| Pour-on solution | |
|---|---|
| compound of Table 1 | 30.00 g |
| sodium dioctylsulfosuccinate | 3.00 g |
| benzyl alcohol | 35.46 g |
| ethylene glycol monomethyl ether | 35.46 g |
| | 103.92 g = 100 ml |

With vigorous stirring, the active ingredient is dissolved in the major part of the mixture of the two solvents. The sodium dioctylsulfosuccinate is subsequently dissolved in the resultant solution, with heating if necessary, and the rest of the solvent mixture is added.

What is claimed is:

1. A compound of formula I

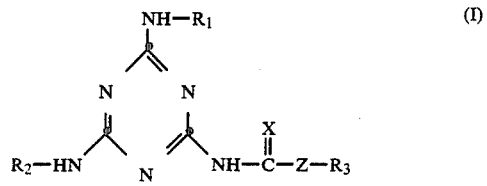

wherein $C_3$–$C_6$
  $R_1$ is alkyl or $C_3$–$C_6$cycloalkyl;
  $R_2$ is hydrogen, $C_1$–$C_6$alkyl, $C_3$–$C_6$cycloalkyl or the group —C(X)—$ZR_3$;
  $R_3$ is $C_1$–$C_6$alkyl, $C_1$–$C_6$haloalkyl, $C_2$–$C_4$alkenyl or $C_2$–$C_4$haloalkenyl;
  X is oxygen or sulfur; and
  Z is oxygen or sulfur;
or an acid addition salt thereof.

2. A compound I according to claim 1, wherein
  $R_1$ is $C_3$alkyl or cyclopropyl;
  $R_2$ is hydrogen, $C_1$–$C_3$alkyl, cyclopropyl or C(O)$OR_3$;
  $R_3$ is $C_1$–$C_4$alkyl, $C_1$–$C_4$chloroalkyl, $C_2$–$C_4$alkenyl or $C_2$–$C_4$haloalkenyl; and
  X and Z are oxygen.

3. A compound I according to claim 2, wherein
  $R_1$ is isopropyl or cyclopropyl;
  $R_2$ is hydrogen or $C_1$–$C_3$alkyl;
  $R_3$ is methyl, ethyl, n-propyl, n-butyl or $C_2$–$C_4$alkenyl; and
  X and Z are oxygen.

4. A compound I according to claim 3, selected from the series consisting of 2-cyclopropylamino-4-amino-6-allyloxycarbonylamino-s-triazine and the acid addition salts thereof,
2-isopropylamino-4-amino-6-allyloxycarbonylamino-s-triazine and the acid addition salts thereof,
2-cyclopropylamino-4-amino-6-methoxycarbonylamino-s-triazine and the acid addition salts thereof,
2-cyclopropylamino-4-amino-6-ethoxycarbonylamino-s-triazine and the acid addition salts thereof,
2-cyclopropylamino-4-amino-6-n-butoxycarbonylamino-s-triazine and the acid addition salts thereof.

5. A composition for controlling pests which are animals or plants, which composition contains as active ingredient at least one compound of the formula $$\begin{array}{c} NH-R_1 \\ \diagup \\ N \quad N \\ \| \quad \| \quad X \\ R_2-HN \quad N \quad NH-\overset{\|}{C}-Z-R_3 \end{array} \quad (I)$$

wherein
R$_1$ is C$_3$–C$_6$alkyl or C$_3$–C$_6$cycloalkyl;
R$_2$ is hydrogen, C$_1$–C$_6$alkyl, C$_3$–C$_6$cycloalkyl or the group —C(X)—ZR$_3$;
R$_3$ is C$_1$–C$_6$alkyl, C$_1$–C$_6$haloalkyl, C$_2$–C$_4$alkenyl or C$_2$–C$_4$haloalkenyl;
X is oxygen or sulfur; and
Z is oxygen or sulfur;
or an acid addition salt thereof, together with customary formulation assistants.

6. A method of controlling harmful insects or ectoparasites or endoparasites, which method comprises applying to the insect or parasite or to the locus thereof an insecticidally or parasiticidally effective amount of a compound $$\begin{array}{c} NH-R_1 \\ \diagup \\ N \quad N \\ \| \quad \| \quad X \\ R_2-HN \quad N \quad NH-\overset{\|}{C}-Z-R_3 \end{array} \quad (I)$$

wherein
R$_1$ is C$_3$–C$_6$alkyl or C$_3$–C$_6$cycloalkyl;
R$_2$ is hydrogen, C$_1$–C$_6$alkyl, C$_3$–C$_6$cycloalkyl or the group —C(X)—ZR$_3$;
R$_3$ is C$_1$–C$_6$alkyl, C$_1$–C$_6$haloalkyl, C$_2$–C$_4$alkenyl or C$_2$–C$_4$haloalkenyl;
X is oxygen or sulfur; and
Z is oxygen or sulfur;
or of an acid addition salt thereof.

7. A method according to claim 6, which comprises applying the compound I orally to the productive livestock in order to treat the excreted faeces.

8. A method according to claim 6, which comprises applying the compound I to the excreted faeces.

9. A composition according to claim 5, containing a compound wherein R$_1$ is C$_3$alkyl or cyclopropyl; R$_2$ is hydrogen, C$_1$–C$_3$alkyl, cyclopropyl or C(O)OR$_3$; R$_3$ is C$_1$–C$_4$alkyl, C$_1$–C$_4$-chloroalkyl, C$_2$–C$_4$alkenyl or C$_2$–C$_4$haloalkenyl; and X and Z are oxygen.

10. A composition according to claim 5, containing a compound wherein R$_1$ is isopropyl or cyclopropyl; R$_2$ is hydrogen or C$_1$–C$_3$alkyl; R$_3$ is methyl, ethyl, n-propyl, n-butyl or C$_2$–C$_4$alkenyl; and X and Z are oxygen.

11. A composition according to claim 5, containing a compound selected from the group consisting of:
2-cyclopropylamino-4-amino-6-allyloxycarbonylamino-s-triazine;
2-isopropylamino-4-amino-6-allyloxycarbonylamino-s-triazine;
2-cyclopropylamino-4-amino-6-methoxycarbonylamino-s-triazine;
2-cyclopropylamino-4-amino-6-ethoxycarbonylamino-s-triazine;
2-cyclopropylamino-4-amino-6-n-butoxycarbonylamino-s-triazine; and
the acid addition salts thereof.

* * * * *